United States Patent [19]
Dinsmore

[11] Patent Number: 6,065,354
[45] Date of Patent: May 23, 2000

[54] SPINDLE MOTOR FIXTURE FOR OUTGASSING SYSTEM

[75] Inventor: Michael Paul Dinsmore, Longmont, Colo.

[73] Assignee: Seagate Technology, Inc., Scotts Valley, Calif.

[21] Appl. No.: 09/345,660

[22] Filed: Jun. 30, 1999

Related U.S. Application Data

[63] Continuation-in-part of application No. 09/315,310, May 20, 1999
[60] Provisional application No. 60/135,462, May 24, 1999.

[51] Int. Cl.$^7$ .................................................. G01N 1/00
[52] U.S. Cl. ...................................... 73/863.12; 73/865.6
[58] Field of Search ........................... 73/863.11, 863.12, 73/863.21, 865.9, 865.6

[56] References Cited

U.S. PATENT DOCUMENTS

| | | |
|---|---|---|
| 5,363,707 | 11/1994 | Augenblick et al. . |
| 5,646,334 | 7/1997 | Scheppers et al. . |
| 5,708,219 | 1/1998 | Scheppers et al. . |
| 5,753,791 | 5/1998 | Scheppers et al. . |
| 5,773,707 | 6/1998 | Scheppers et al. . |
| 5,792,423 | 8/1998 | Markelov . |
| 5,859,356 | 1/1999 | Scheppers et al. . |
| 5,869,741 | 2/1999 | Scheppers et al. . |
| 5,974,902 | 11/1999 | Scofield ................................ 73/865.6 |

*Primary Examiner*—Robert Raevis
*Attorney, Agent, or Firm*—Merchant & Gould P.C.; John B. Phillips; Homer L. Knearl

[57] ABSTRACT

An apparatus for retaining a spindle motor during an outgassing test includes a body formed from an inert material and having an interior chamber for receiving a base of the spindle motor. Fasteners secure the spindle motor to the body to seal the interior chamber and prevent the spindle motor base from outgassing any compounds during the outgassing test. An electrical pad attached within the interior chamber contacts an electrical connector on the base of the spindle motor. An electrical wire attaches the electrical pad to a combination power source and motor controller for operating the spindle motor. The body and the attached spindle motor are placed within a test container and the electrical wire is passed through both the body and the test container for attachment to the power source and motor controller. The electrical wire includes an inert coating to prevent the electrical wire from impacting the results of the outgassing test.

20 Claims, 8 Drawing Sheets

SPINDLE MOTOR FIXTURE FOR OUTGASSING SYSTEM

RELATED APPLICATIONS

This application is a continuation-in-part of U.S. patent application 09/315,310, entitled DYNAMIC HEADSPACE OUTGASSING SYSTEM, filed May 20, 1999. This application also claims the benefit of U.S. Provisional Application Ser. No. 60/135,462, entitled DYNAMIC SPINDLE MOTOR FIXTURE, filed May 24, 1999.

FIELD OF THE INVENTION

The present invention relates to collecting chemicals and chemical compounds outgassed by a disc drive spindle motor. More particularly, the present invention relates to a system for collecting outgassed compounds by fixing the spindle motor within a testing container so that only a portion of the motor is exposed to the interior of the container and so that the motor may be operated within the testing container in a manner representative of operation within a disc drive.

BACKGROUND OF THE INVENTION

It is well known that complex electromechanical devices, such as computer disc drives, can be harmed by foreign substances which come into contact with vital components of the device. For example, dirt or dust particles which accumulate on the platters of a disc drive can damage the read/write head of the drive causing a "crash." Thus, such devices are typically manufactured within a clean room environment and are sealed prior to leaving the clean room to reduce or prevent the possibility of such contamination.

However, the current breed of disc drives spin much faster and are more densely packed with data than prior drives. These speed and size increases require that the read/write heads fly very close to the surface of the disc platters (on the order of a micron). In light of these very low fly heights, it is possible for matter smaller than common dust or smoke particles to cause head/disc crashes. Indeed, even chemicals or chemical compounds which are outgassed by the different components of the disc drive may be sufficiently large to interfere with the drive heads.

Although some disc drive components outgas chemicals and chemical compounds while the drive is inactive, the level of outgassing typically increases when the drive is operating and the components are exposed to high temperatures. These outgassed chemicals and chemical compounds are easily transported throughout the drive (due to the rotation of the disc platters and the resulting air currents within the drive) where they typically bond to the substrate that coats the disc platters. In addition to physically interfering with the drive heads during operation of the drive, some aggressive outgassed compounds (e.g., adhesives) may react chemically with the drive heads during periods of inactivity when the heads are in direct contact with the disc platters. Such chemical reactions cause stiction between the heads and the disc platters which further contributes to early disc drive failure.

Thus, it is important for disc drive manufacturers to carefully inspect all of the components which make up the drive for the presence of outgassed compounds. Examples of such components within a disc drive include voice coil motors, coil bobbins, magnets, read/write heads, adhesives and labels. One specific disc drive component that may contribute greatly to the total outgassing of a disc drive is the spindle motor.

FIG. 1 illustrates a typical prior art spindle motor 20. The motor 20 includes a base 22 which is fixed to a base plate 24 (FIG. 2) of a disc drive 26. A hub 28 (FIG. 1) of the spindle motor 20 rotates on a bearing (not shown) about a shaft 30 connected to the base 22. In this manner, the hub 28 is free to rotate in relation to the base 22 of the spindle motor 20. The base 22 typically includes electrical windings (not shown) while the hub 28 typically includes magnets (not shown) which interact with the magnetic field created when an electrical current passes through the windings (not shown) within the base 22. Thus, the base 22 acts as a stator while the hub 28 acts as a rotor of the spindle motor 20.

One or more disc platters 32 (FIG. 2) are attached to rotate with the hub 28 about the fixed shaft 30. A separate voice coil motor 34 operates to move one or more arms 36 over the spinning disc platters 32 so that magnetic read/write heads 38 can access any part of the disc platters 32. In current disc drives, the spindle motor 20 may be required to spin at speeds up to 10,000 revolutions per minute (RPM). This high speed operation, together with the large number of components which make up a spindle motor (e.g., magnets, wiring, bearings, adhesive seals, etc.), causes the spindle motor 20 to outgas a variety of compounds. Although the spindle motor 20 outgasses compounds even when the motor 20 is idle, the outgassing levels increase dramatically during operation of the spindle motor. Specifically, many of the components within the spindle motor 20 may outgas compounds which are normally retained within the motor 20 while the motor is at rest. However, when the motor 20 spins up to an operating speed of 5,000 to 10,000 RPM, centrifugal force tends to expel these compounds from the interior of the motor 20 to the interior of the drive 26.

Unfortunately, prior outgassing test systems typically test the spindle motor in an idle or non-operative state. Specifically, one type of outgassing test, hereafter referred to as "static headspace sampling," entails placing a component (such as the idle spindle motor 20 shown in FIG. 1) within a sealed container and holding the component at an elevated temperature until the outgassed compounds reach a state of equilibrium within the headspace. The term "headspace" is utilized herein to refer to the space within the sealed container which is not taken up by the tested component itself. The sealed container typically includes an open top sealed by a septum to allow a needle to penetrate the headspace and withdraw a sample of the equilibrated headspace. This sample is then analyzed using known techniques and equipment such as a gas chromatograph and a mass spectrometer to determine the composition of the different outgassed compounds. However, while testing the spindle motor 20 at an elevated temperature may simulate the heat which is generated by an operating spindle motor 20, any additional compounds outgassed at the elevated temperatures will likely remain confined within the interior of the non-operative motor itself.

One alternative to the static headspace sampling test entails placing the component to be tested within a test container and then passing an inert gas through the container during the course of the test to continuously flush outgassed compounds from the container. This is referred to as a dynamic headspace outgassing test. However, the dynamic gas flow applied to the test container during the dynamic headspace outgassing test is not typically strong enough to expel outgassed compounds from the confines of the idle spindle motor 20. Thus, regardless of whether a static or a dynamic outgassing procedure is used to test the spindle motor 20, neither test provides a sufficiently accurate or representative indication of the types and amounts of outgassed compounds which an operative (i.e., spinning) spindle motor 20 produces and expels within the interior of a functioning disc drive 26.

A further concern with prior art spindle motor outgassing tests is that the entire spindle motor 20 (FIG. 1) is typically placed within the testing container (regardless of whether the container is used in a static or a dynamic testing system). However, FIGS. 2 and 3 illustrate that only a portion of the spindle motor 20 is exposed to the interior of the disc drive 26 so that testing the entire spindle motor 20 may lead to the detection of outgassed compounds which would not normally be found within the interior of the drive 26 (i.e., a false positive reading).

FIG. 2 illustrates an exploded view of a disc drive 26 showing the base plate 24 of the drive together with a top cover 40 and a printed circuit board assembly (PCBA) 42 which are attached to opposite sides of the base plate 24. The top cover 40 fits over the voice coil motor 34, the arms 36, the disc platter(s) 32 and the spindle motor 20 to form a substantially sealed interior volume of the disc drive 26. The disc platters 32 are cut away in FIG. 2 to better illustrate the spindle motor 20 mounted to the disc drive base plate 24. The base plate 24 includes an opening (not shown) for receiving the base 22 of the spindle motor while an outwardly protruding annular flange 46 of the base 22 (best shown in FIG. 1) is preferably attached to a top surface 48 of the disc drive base plate 24 by a plurality of screws 50. Attached in this manner, the base 22 of the spindle motor 20 extends below the base plate 24 of the disc drive, as shown in FIG. 3, and thus is not exposed to the interior volume of the disc drive 26.

One significant element of the spindle motor 20 which extends below the base plate 24 of the disc drive 26 is the electrical connector 52 (FIG. 1) which provides power for operating the spindle motor 20. Specifically, the electrical connector 52 is attached to a lower portion of the spindle motor base 22 so that a number of electrical leads 54 extend radially outwardly from the base 22 below the annular flange 46. The electrical leads 54 are positioned to contact matching electrical pads 56 (FIG. 2) on a top surface 58 of the PCBA 42 as the base 22 of the spindle motor 20 extends through a circular opening 60 formed in the PCBA 42. The electrical pads 56 supply power to the connector 52 for operating the spindle motor 20 once the PCBA 42 is connected to a power supply/motor controller (not shown). Furthermore, the connector 52 is typically attached to the spindle motor base 22 by an adhesive material, and the presence of the connector 52 and the adhesive material within the prior art testing container frequently contributes false positive readings to prior art outgassing tests.

Thus, prior art outgassing tests of disc drive spindle motors produce inaccurate or unrepresentative results for two primary reasons. First, the motors are typically tested in an idle state where the hub or "rotor" 28 is not rotating so that outgassed compounds within the motor 20 are not expelled into the headspace of the testing container. Second, the motors are typically tested as a whole so that the outgassing results include contributions from components of the motor 26 which are not typically exposed to the interior volume of the disc drive 26.

It is with respect to these and other background considerations, limitations and problems that the present invention has evolved.

SUMMARY OF THE INVENTION

The present invention relates to a system for fixing a spindle motor within a testing container so that only a portion of the spindle motor is exposed to the interior of the testing container and, in one embodiment, to operate the spindle motor within the testing container in a manner representative of operation within a disc drive.

In accordance with one embodiment of the present invention, an apparatus is provided for retaining a spindle motor during an outgassing test. The spindle motor typically includes an annular base and a hub adapted to rotate relative to the annular base. The apparatus includes a body with an interior chamber for receiving the annular base of the spindle motor. Once the spindle motor base has been inserted within the interior chamber, fasteners secure the spindle motor to the body and form a substantially airtight seal within the interior chamber to prevent the spindle motor base from outgassing any compounds during the outgassing test. The body may be formed from an inert material to prevent the body from impacting the results of the outgassing test.

In another embodiment of the present invention, the apparatus further includes an electrical pad attached within the interior chamber for contacting an electrical connector on the base of the spindle motor. An electrical wire is attached at one end to the electrical pad within the interior chamber and extends outside of the interior chamber to connect the electrical pad to a combination power source and motor controller for operating the spindle motor.

The present invention can also be implemented as an apparatus for collecting outgassed compounds from a spindle motor. One embodiment of the apparatus including a body formed from an inert material and defining an interior chamber for receiving the annular base of the spindle motor. Once the spindle motor base has been inserted within the interior chamber, fasteners secure the spindle motor to the body and form a substantially airtight seal within the interior chamber. A test container defines an interior volume for receiving both the body and the attached spindle motor, and the airtight seal prevents the spindle motor base from outgassing any compounds within the interior volume of the test container. The body may be formed from an inert material to prevent the body from outgassing any compounds, as well as to prevent the body from reacting with any compounds outgassed by the spindle motor, within the test container.

In another embodiment of the present invention, the apparatus further includes an electrical pad attached within the interior chamber for contacting an electrical connector on the base of the spindle motor. An electrical wire is attached at one end to the electrical pad within the interior chamber and extends outside of the interior chamber of the body and outside of the interior volume of the test container to connect the electrical pad to a combination power source and motor controller for operating the spindle motor.

The present invention can further be implemented as an apparatus for collecting outgassed compounds from a spindle motor including a test container and means for retaining the spindle motor in the test container and for preventing the annular base and the electrical connector from outgassing compounds within the test container. In another embodiment of the present invention, the apparatus further includes means for providing power to the spindle motor to operate the spindle motor within the test container.

These and various other features as well as advantages which characterize the present invention will be apparent from a reading of the following detailed description and a review of the associated drawings.

DETAILED DESCRIPTION OF THE PREFERRED EMBODIMENTS

Figure 1:
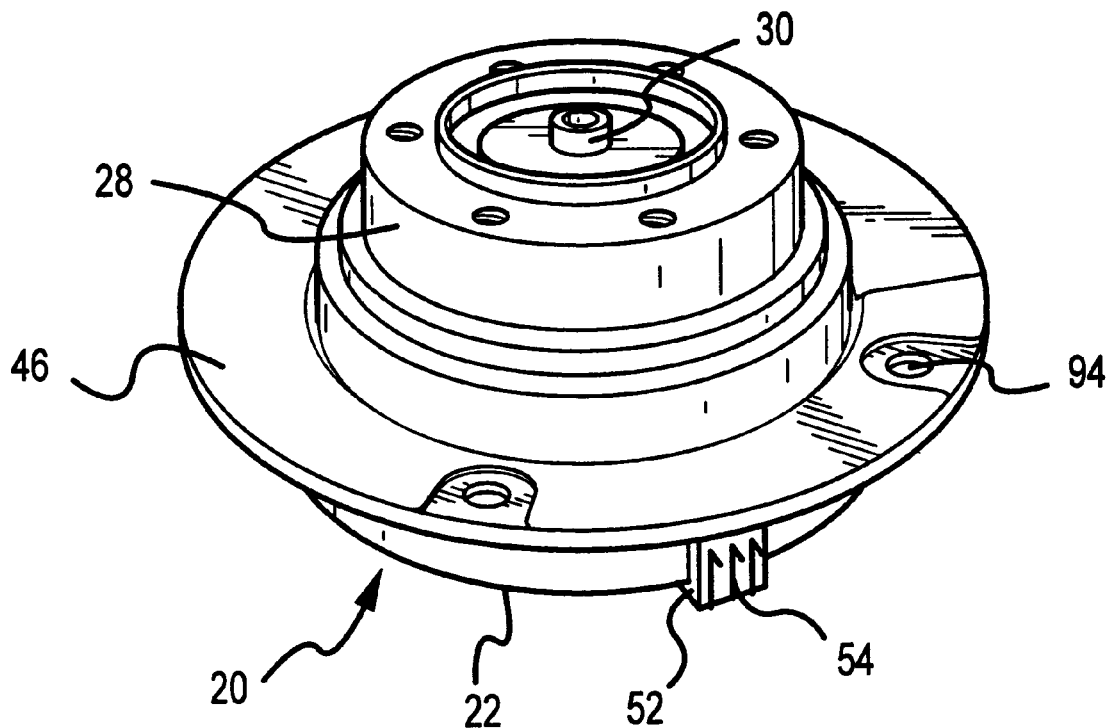
FIG. 1 is an isometric view of a prior art spindle motor for a disc drive.
Figure 3:
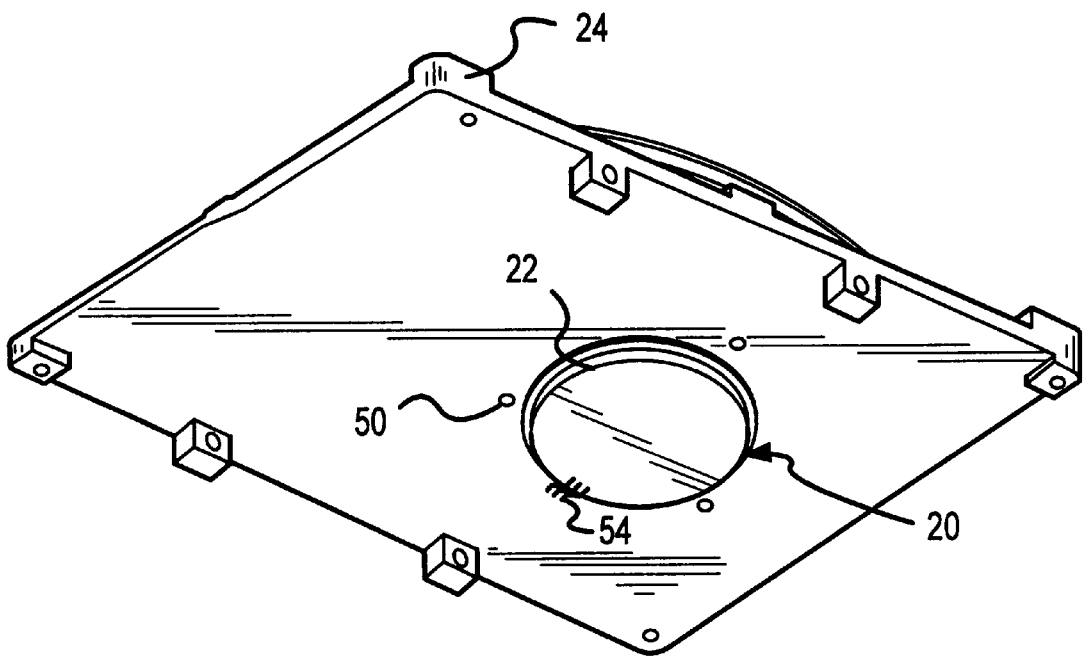
FIG. 3 is an isometric bottom view of a base plate of the prior art disc drive shown in FIG. 2 illustrating a portion of the spindle motor protruding through an opening formed in the base plate.
Figure 4:
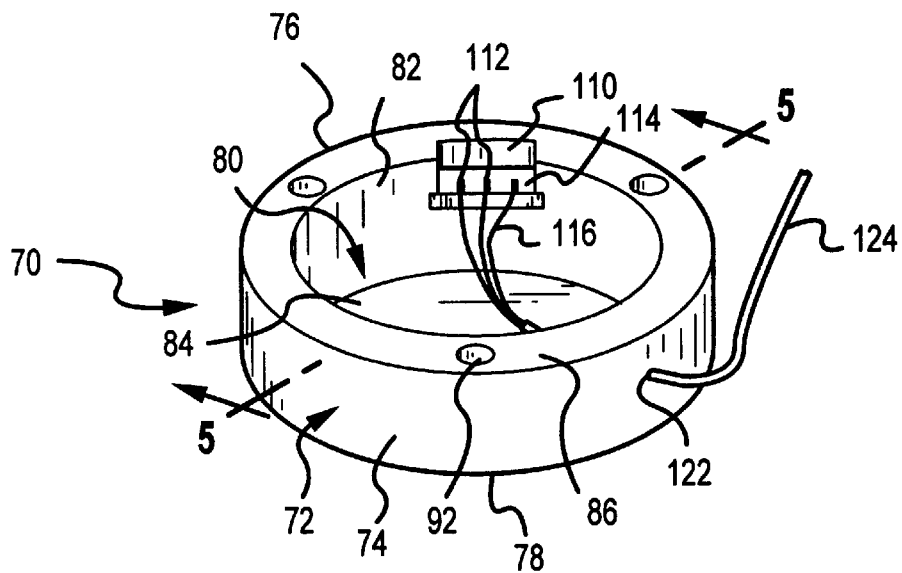
FIG. 4 is an isometric view of a spindle motor fixture for receiving the spindle motor shown in FIG. 1 in accordance with a preferred embodiment of the present invention.

FIG. 4 illustrates a preferred embodiment of a spindle motor fixture 70 of the present invention. The spindle motor fixture 70 is adapted to accommodate a spindle motor 20, as shown in FIG. 1, and to provide power to the electrical connector 52 on the motor 20 to allow operation of the motor 20 during an outgassing test. The base 22 of the spindle motor 20 is recessed within the spindle motor fixture 70 as described below (FIGS. 7–9) to simulate the actual portion of the spindle motor 20 which is exposed within the disc drive 26 (see FIGS. 2 and 3).

Figure 8:
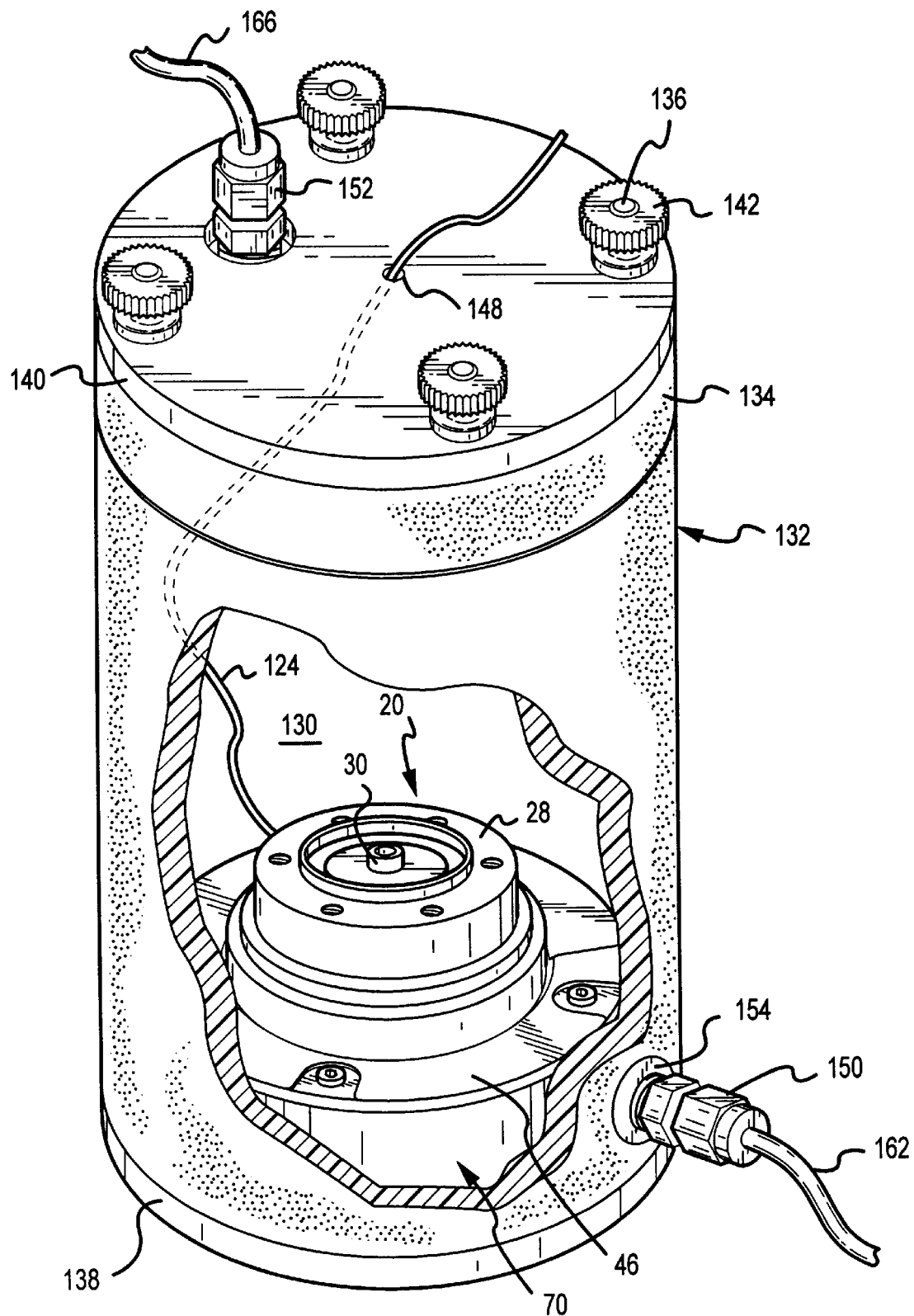
FIG. 8 is an isometric view of the spindle motor fixture and the attached spindle motor positioned within a bottom portion of a test container used to perform dynamic headspace outgassing tests in accordance with a preferred embodiment of the present invention.
Figure 9:
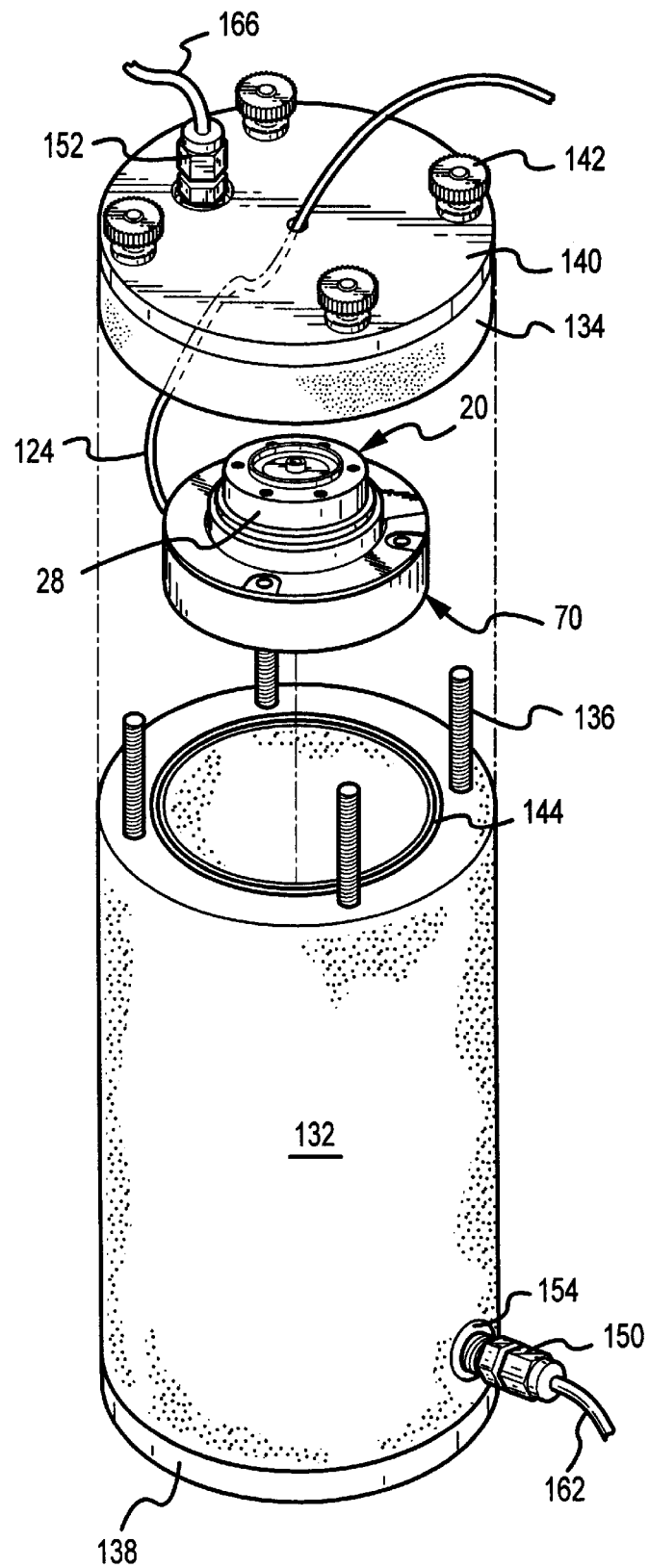
FIG. 9 is an exploded view of the test container and the spindle motor fixture with attached spindle motor shown in FIG. 8.
Figure 10:
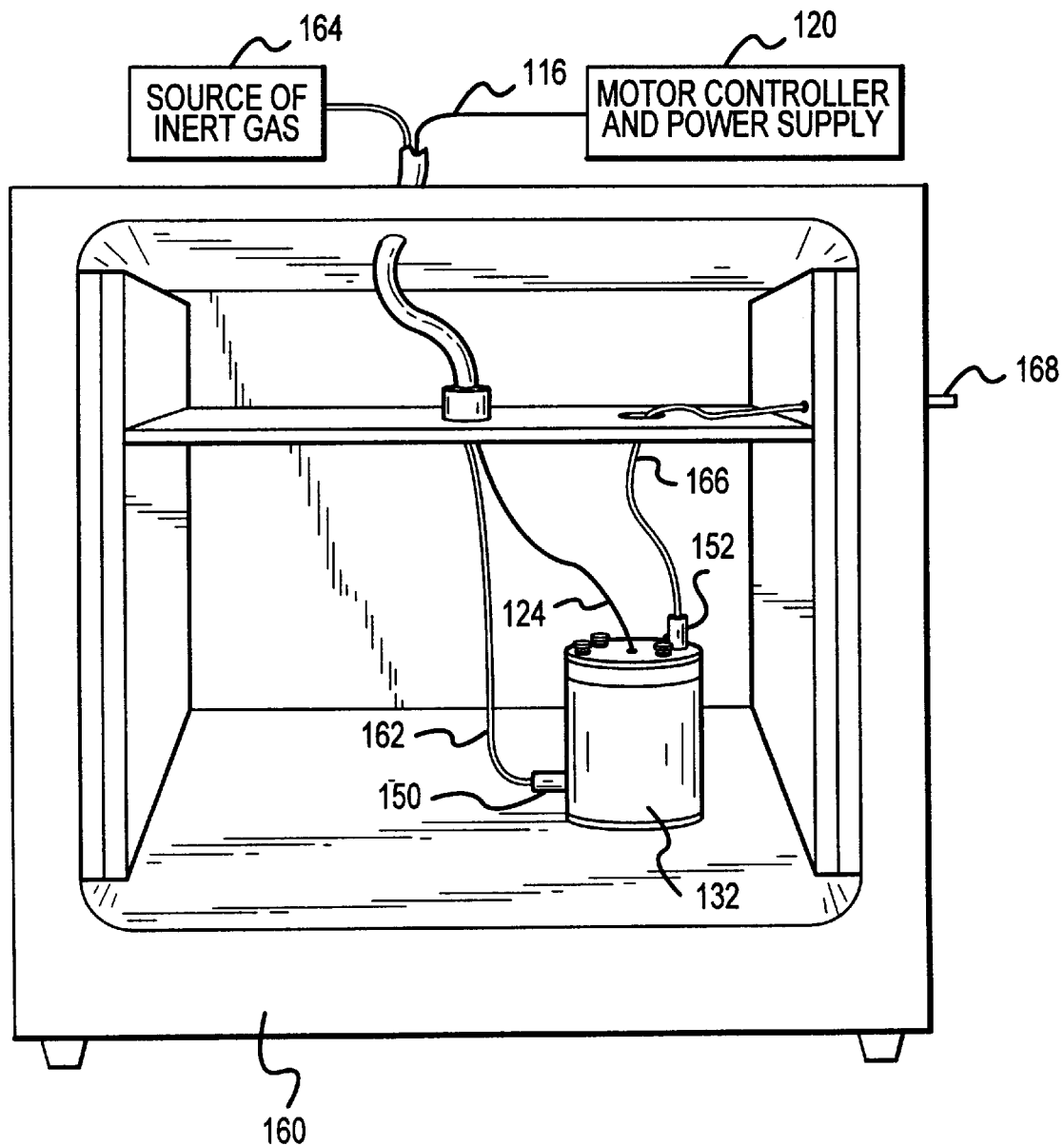
FIG. 10 is a perspective view of an oven containing the test container with the spindle motor fixture and attached spindle motor inserted therein, and further illustrating the connection of gas inflow and outflow lines to the test container and the connection of the spindle motor fixture to a power supply/motor controller for operating the spindle motor.

Although the preferred embodiment of the spindle motor fixture 70 is illustrated for use with a particular dynamic headspace outgassing system illustrated in FIGS. 8–10, it is understood that the spindle motor fixture 70 may be beneficially used with other types of outgassing systems, including the static headspace sampling system described above. That is, any outgassing system which normally tests a spindle motor in an idle or non-operative state would benefit from using the spindle motor fixture 70 to improve the accuracy of the outgassing test results. Thus, the illustration and following description of the use of the preferred embodiment of the spindle motor fixture 70 with the dynamic headspace outgassing system of parent U.S. patent application Ser. No. 09/315,310 should not be viewed as a limitation on the present invention.

The spindle motor fixture 70 preferably includes a substantially cylindrical body 72 formed from an inert material such as Teflon. The cylindrical body 72 includes an outer surface 74, a top end 76 and a bottom end 78. A bore formed from the top end 76 of the body 72 defines an interior chamber 80 for receiving the base 22 of the spindle motor 20. The interior chamber 80 is open at the top end 76 and is bounded by a cylindrical interior wall 82 and an interior bottom surface 84.

An annular rim 86 (FIG. 4) surrounds the open top end 76 of the chamber 80, while an exterior bottom surface 88 (FIGS. 5 and 6) of the Teflon body 72 preferably includes an annular groove 90 (FIG. 5) formed therein to underlie the annular rim 86 at the top of the body 72. A plurality of through holes 92 (FIGS. 4–6) are preferably formed lengthwise between the annular rim 86 and the annular groove 90 of the body 72. The holes 92 are spaced equidistantly around the rim 86 as shown in FIG. 4 and are preferably aligned with holes 94 formed in the annular flange 46 of the spindle motor 20 to allow mounting screws 96 to attach the spindle motor 20 onto the spindle motor fixture 70, as described below.

Figure 7:
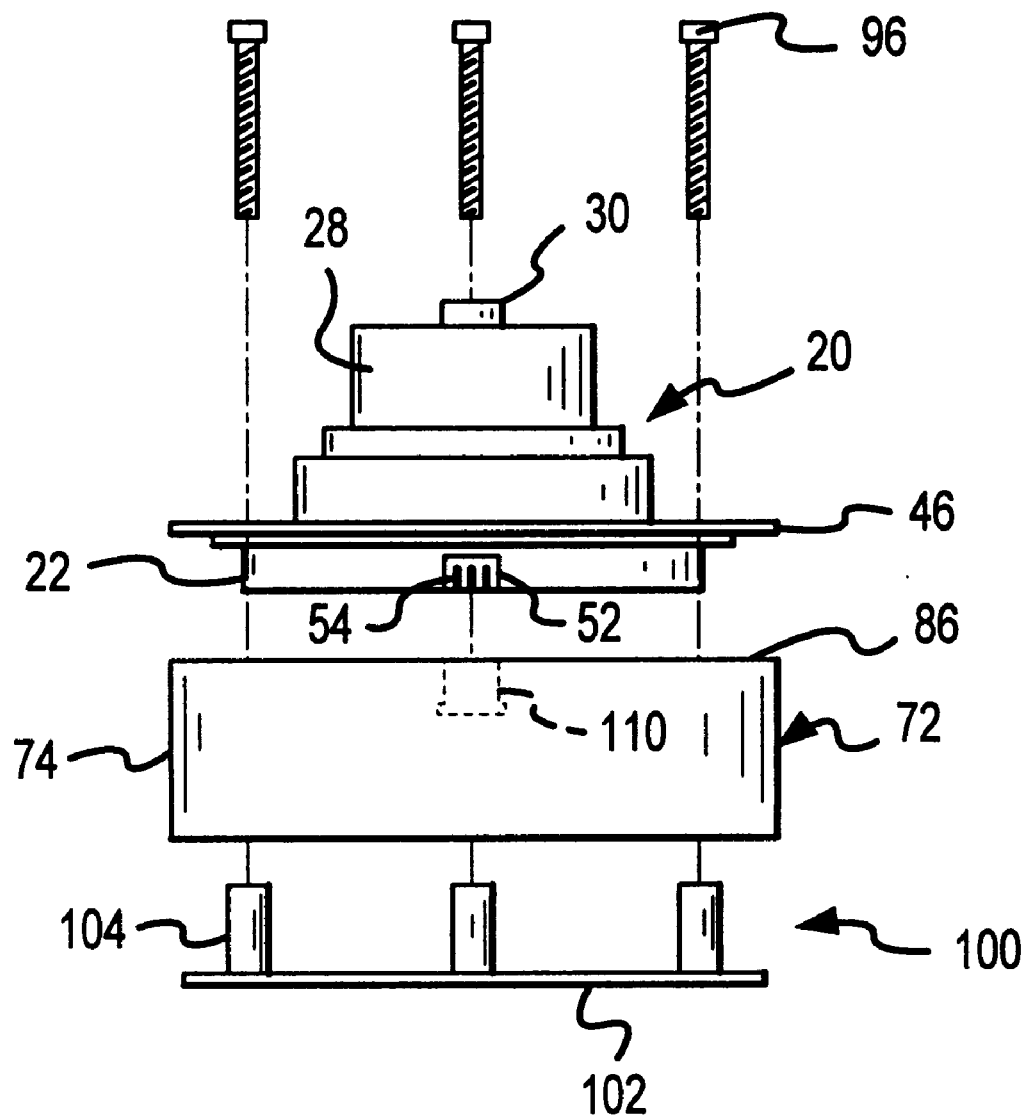
FIG. 7 is an exploded view of the spindle motor fixture shown in FIG. 4 together with the spindle motor shown in FIG. 1.

Due to the malleable nature of Teflon, and particularly the tendency of Teflon to change shape when heated, the spindle motor fixture 70 includes a separate mounting ring 100 (FIG. 7) for anchoring the mounting screws 96. The mounting ring 100 is preferably formed from stainless steel and includes an annular base 102 and three cylindrical posts 104 extending vertically upward from the annular base 102. The three cylindrical posts 104 are spaced equidistantly about the annular base 102 and are preferably aligned with the through holes 92 formed in the body 72 of the spindle motor fixture 70. An outer diameter of the cylindrical posts 104 is substantially equal to a diameter of the through holes 92 so that the posts 104 of the mounting ring 100 may be inserted into the through holes 92 from the bottom end 78 of the Teflon body 72, as shown in FIG. 7. An interior surface 106 (FIG. 5) of each cylindrical post 104 is threaded to receive an end of the mounting screws 96.

Figure 5:
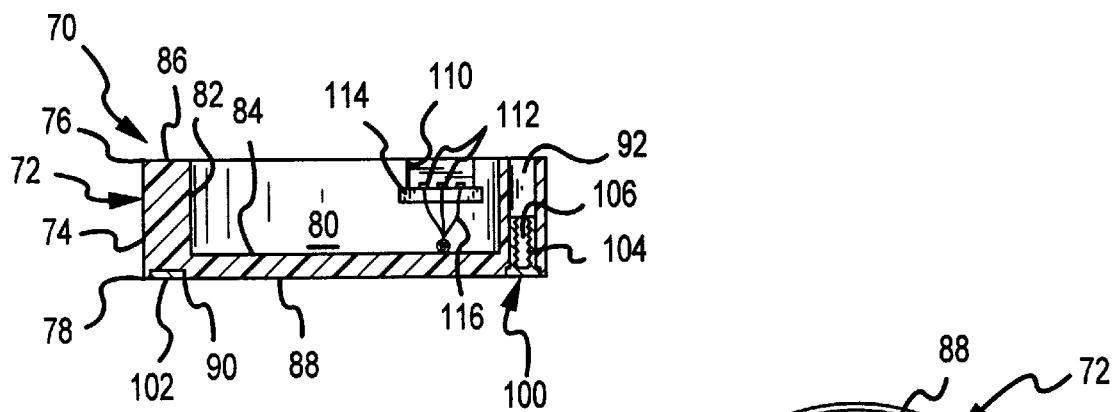
FIG. 5 is a section view taken substantially along the line 5—5 in FIG. 4.
Figure 6:
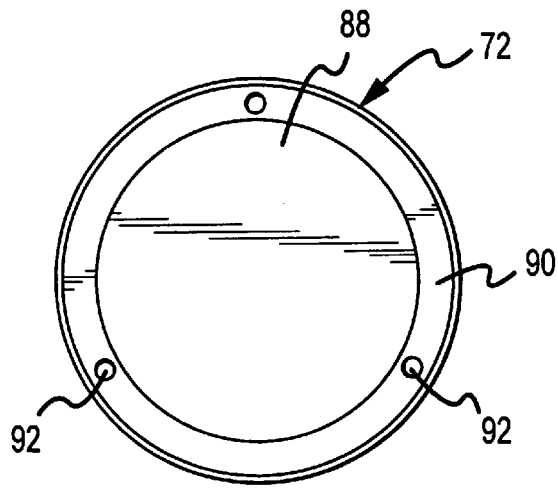
FIG. 6 is a bottom view of the spindle motor fixture shown in FIG. 4 without an attached mounting ring to illustrate the detail of the bottom surface of the fixture body.

The annular base 102 of the mounting ring 100 is preferably dimensioned to fit flush within the annular groove 90 on the bottom surface 88 of the body so that the annular base 102 is effectively recessed within the exterior bottom surface 88, as shown in FIG. 5. Recessing the stainless steel mounting ring 100 in this manner is important for minimizing possible sources of contamination during the outgassing test, as described below.

Although the base 22 of the spindle motor 20 is substantially cylindrical in shape as shown in FIGS. 1 and 3, the electrical connector 52 protrudes radially outward from the base 22 as shown in FIG. 1. Thus, the interior chamber 80 of the spindle motor fixture 70 preferably includes a cut-out or notched region 110 (FIGS. 4 and 5) to accommodate the protruding electrical connector 52. The notched region 110 preferably extends from the annular rim 86 and proceeds down the cylindrical inner surface 82 of the chamber 80 as shown in FIGS. 4 and 5. A bottom portion of the notched region 110 preferably widens into a horizontal ledge 111 for supporting a plurality of electrical pads 112 adapted to engage the electrical leads 54 on the spindle motor electrical connector 52. In the preferred embodiment shown in FIGS. 4 and 5, the pads 112 are fixed to a small circuit board 114 which, in turn, fits atop the widened horizontal ledge 111 at the bottom of the notched region 110. Of course, one skilled in the art may conceive of alternative means for securing the electrical pads 112 within the cut-out or notched region 110 to ensure secure contact between the pads 112 and the leads 54 of the spindle motor connector 52.

In essence, the electrical pads 112 (FIGS. 4 and 5) simulate the pads 56 (FIG. 2) on the PCBA 42 which normally contact the leads 54 of the connector 52 when the spindle motor 20 is installed within a disc drive 26. Electrical wires 116 (FIGS. 4 and 5) attached to each pad 112 are connected to a power supply/motor controller 120 (FIG. 10) as described in greater detail below. The electrical wires 116 preferably extend along the interior bottom surface 84 of the chamber 80 where they pass through an opening 122 formed between the inner surface 82 and the outer surface 74 of the body 72 of the spindle motor fixture 70. The wires 116 are preferably surrounded by a Teflon sheath 124 (FIG. 4) so that only the Teflon material and not the wires 116 themselves are exposed to the environment outside of the chamber 80.

FIG. 7 illustrates the attachment of the spindle motor 20 to the spindle motor fixture 70. The base 22 of the motor 20 is first inserted within the chamber 80 of the motor fixture 70 so that the electrical connector 52 is aligned with the notched region 110. The base 22 is lowered into the chamber 80 until the annular flange 46 surrounding the base 22 contacts the annular rim 86 at the top end 76 of the fixture 70. The depth of the horizontal ledge 111 along the notched region 110 of the chamber 80 preferably positions the small circuit board 114 so that the electrical pads 112 contact the electrical leads 54 of the connector 52 once the annular flange 46 contacts the annular rim 86. Once positioned as described above, the mounting screws 96 are inserted through both the holes 94 in the annular flange 46 of the motor 20 as well as the holes 92 formed in the Teflon body 72 of the spindle motor fixture 70. The ends of the mounting screws 96 are received within the cylindrical threaded posts 104 so that tightening the screws 96 causes the motor 20 and the stainless steel mounting ring 100 to be drawn together. Thus, tightening the screws 96 produces two beneficial results. First, the mounting ring 100 is drawn upward to the maximum extent possible to ensure the ring 100 is recessed within the annular groove 90 in the bottom surface 88 of the fixture 70. Second, the annular flange 46 on the spindle motor is forced down to bear against the relatively soft annular rim 86, thereby forming a substantially airtight seal around the interior chamber 80. Although the chamber 80 does include the opening 122 for allowing the electrical wires 116 to pass outside of the chamber 80, the Teflon sheath 124 surrounding the wires 116 helps to seal the opening 122, thereby maintaining a substantially airtight seal within the chamber 80.

Thus, the assembly of the spindle motor 20 with the spindle motor fixture 70 serves to conceal the base 22 and the connector 52 of the spindle motor 20 within the substantially airtight chamber 80 of the fixture 70. In this manner, the spindle motor fixture 70 accurately simulates the connection of the spindle motor 20 within a disc drive 26 since the same portion of the motor 20 is exposed in both instances. Furthermore, the use of Teflon to both form the body 72 of the spindle motor fixture 70 and to form the sheath 124 for wrapping the electrical wires 116 ensures that the fixture 70 itself will not contaminate the outgassing test since Teflon is substantially inert even at the elevated temperatures typically used for outgassing tests. Of course, while Teflon is described as the preferred material for both the fixture body 72 and the electrical wire sheath 124, one skilled in the art may utilize other substantially inert materials in place of Teflon.

Once the spindle motor 20 and the spindle motor fixture 70 are assembled as shown in FIG. 7, the combination motor 20 and fixture 70 is preferably inserted within a testing container for the purposes of conducting an outgassing test. One preferred use of the spindle motor fixture 70 to test a spindle motor 20 is with the dynamic headspace outgassing system illustrated in FIGS. 8–10 and described in greater detail in parent U.S. patent application Ser. No. 09/315,310, entitled DYNAMIC HEADSPACE OUTGASSING SYSTEM, filed May 20, 1999, and assigned to the assignee of the present invention, the disclosure of which is hereby incorporated by this reference.

FIGS. 8 and 9 illustrate the spindle motor fixture 70 and the attached spindle motor 20 inserted within a chamber 130 of a Teflon test container 132. The Teflon container 132 essentially comprises an open cylinder similar to but larger than the body 72 of the spindle motor fixture 70 itself. A Teflon top or lid 134 is used to seal the open top of the container 132 once the spindle motor fixture 70 and the attached spindle motor 20 have been inserted within the chamber 130, as shown in FIG. 9. A plurality of threaded rods 136 (FIG. 9) preferably run vertically through the through the container 132 and attach to a steel plate 138 to the bottom of the Teflon container 132. Upper ends of the threaded rods 136 extend through openings (not shown) formed in the Teflon top 134 and through additional aligned openings (not shown) in an upper steel plate 140. Thumb nuts 142 are then threaded onto the rods 136 to bear against the upper steel plate 140 and compress the Teflon top 134 against the open upper end of the Teflon test container 132. An o-ring 144 (FIG. 9) works in conjunction with the relatively malleable Teflon material to ensure an airtight seal between the top 134 and the container 132 once the spindle motor fixture 70 and spindle motor 20 have been inserted within the chamber 130.

Prior to sealing the spindle motor fixture 70 within the chamber 130, the Teflon sheath 124 surrounding the electrical wires 116 is preferably threaded through an opening (not shown) in the Teflon top 134 and a second opening 148 in the upper steel plate 140, as shown in FIG. 9. The electrical wires 116 are then attached to a power supply/motor controller 120 (FIG. 10), as described in greater detail below. It is preferred that a single Teflon top 134 is matched with a particular spindle motor fixture 70 so that the electrical wires 116 and the Teflon sheath 124 can be carefully fitted through the Teflon top 134 in a manner which does not degrade the airtight seal within the chamber 130. Thus, the top 134 is specifically used with the container 132 for testing spindle motors 20 with the spindle motor fixture 70, although another Teflon top (without an opening for the wire sheath 124) may be used with the same container 132 for conducting outgassing tests of other (non-powered) disc drive components.

The outgassing container 132 and top 134 preferably include gas inflow and outflow connectors 150 and 152, respectively. The connectors 150 and 152 each include a threaded end (not shown) which preferably mates with a threaded bushing 154 set within the Teflon material of the container 132 and the top 134. The bushings 154 thus hold the connectors 150 and 152 in fluid communication with a small opening formed through the respective wall of the container 132 and the top 134 to provide access to the interior chamber 130. Additional details regarding the container 132, the top 134 and the connectors 150 and 152 may be found in parent U.S. patent application Ser. No. 09/315,310, although the present invention is not limited to use with the outgas testing container disclosed therein.

One preferred system for conducting the outgassing test of the spindle motor 20 is shown in FIG. 10. The testing container 132 with the spindle motor fixture 70 and attached motor 20 placed therein is preferably placed within a laboratory oven 160 to maintain the test chamber 130 at a predetermined temperature during the course of the outgassing test. A gas inflow line 162 is connected between the inflow connector 150 and a source 164 of inert gas such as a source of substantially pure Nitrogen gas. Similarly, a gas outflow line 166 is attached between the outflow connector 152 on the container and a trap 168 on the exterior of the oven 160. The trap 168 preferably comprises a hollow tube filled with an absorbent such as activated carbon which bonds with any outgassed compounds expelled from the chamber 130 while allowing the inert Nitrogen gas to pass through the tube to the atmosphere.

The outgassing test is conducted by flowing the inert gas through the chamber 130 at a predetermined flow rate for a predetermined time. For example, a flow rate of 50 milliliters/minute for a three-hour test period at an oven temperature of 85 degrees Celsius has been found to provide consistent and repeatable test results. At the conclusion of the outgassing test, the contents of the carbon trap 168 are desorbed and analyzed with standard equipment such as a gas chromatograph and a mass spectrometer to determine the composition of the outgassed chemicals and compounds.

Figure 2:
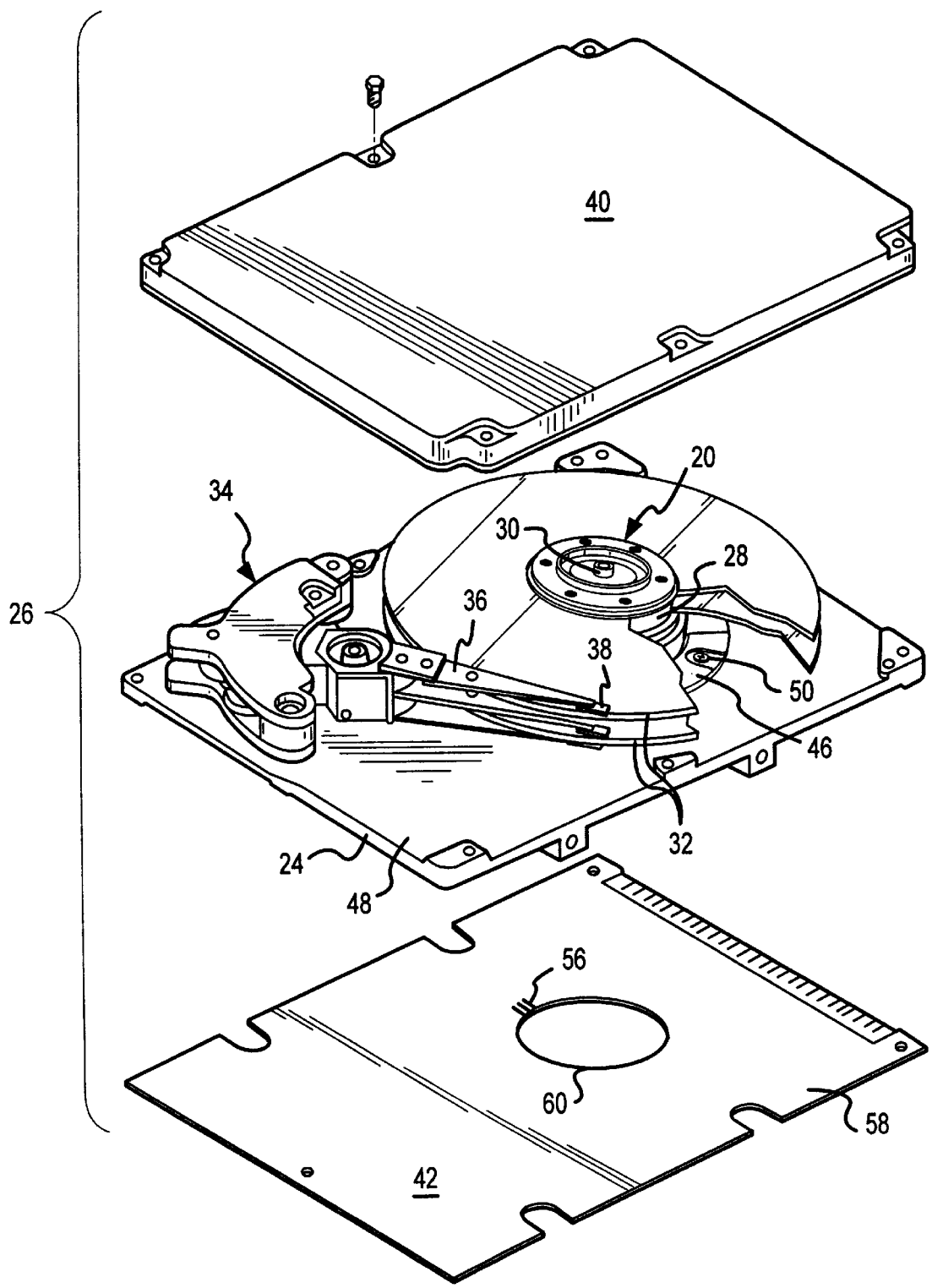
FIG. 2 is an exploded view of a prior art disc drive with a portion cut away to show the connection of the spindle motor within the disc drive.

Regardless of the specific outgas testing system which is utilized (e.g., static or dynamic), the spindle motor fixture 70 ensures that only the desired, representative portion of the spindle motor 20 will be exposed within the test chamber. Using the example of the testing container 132 in FIG. 8, the inert gas flowing through the chamber 130 is exposed to only inert materials (e.g., the Teflon container 132 and top 134, the Teflon body 72 of the fixture 70, and the Teflon wire sheath 124) and to the same upper portion of the motor 20 which is exposed within the disc drive 26 (FIG. 2). Thus, even if the spindle motor 20 is tested in an idle or non-operative state, the ability of the fixture 70 to conceal the base 22 and the electrical connector 52 of the spindle motor enhances the accuracy and representative nature of the results in comparison with prior outgassing tests that place the entire spindle motor 20 in the test container. However, another important benefit of the present invention is the ability to operate the spindle motor 20 during the outgassing test, as described below.

The electrical wires 116 connect the spindle motor 20 to a power supply/motor controller 120 which is located outside of the oven 160, as shown in FIG. 10. The power supply/motor controller 120 supplies the necessary power to spin the "rotor" or hub 28 of the spindle motor 20 at a predetermined rotational velocity. For example, current disc drives typically utilize spindle motor speeds of 5,400, 7,200 or 10,000 RPM. Thus, the power supply/motor controller 120 is preferably capable of supplying the proper power and control signals to the spindle motor 20 to achieve the desired spin rate. Furthermore, the motor controller 120 is preferably specially programmed with "run only" code to allow the motor hub 28 to spin continuously during the multi-hour test without timing out and stopping prior to the end of the test.

The spindle motor fixture 70 thus allows the spindle motor 20 to be operated in a normal matter during the course of the outgassing test. As described above, operation of the spindle motor 20 provides added benefits over simply heating the motor to simulate the operating temperature of the motor 20. Although it is still desirable to place the test container 132 within the oven 160 to simulate the elevated temperature that the disc drive 26 experiences within a computer environment, simply heating the motor 20 can not simulate the centrifugal forces experienced by the motor during operation at high spin rates. Indeed, the following table demonstrates the outgassing results for three different tests of a spindle motor. The three columns of data provide dynamic headspace outgassing data (in nanograms) for testing (1) the entire spindle motor 20 in an idle state (i.e., the prior art method); (2) only the top portion of the idle spindle motor 20 using the spindle motor fixture 70; and (3) only the top portion of the operating spindle motor using the spindle motor fixture 70 and a power supply/motor controller 120 that spins the motor hub 28 at a rate of 5,400 RPM. All tests were run over a three hour period at an oven temperature of 85 degrees Celsius, and each column represents the average of at least three test runs.

| Compound Name | Entire Spindle Motor (Without the Spindle Motor Fixture) (nanograms) | Top Portion Only of Idle Spindle Motor (With the Spindle Motor Fixture) (nanograms) | Top Portion Only of Running Spindle Motor (With the Spindle Motor Fixture) (nanograms) |
|---|---|---|---|
| Glycol Dimethacrylates (TGDMA) | 0 | 0 | 451 |
| Hydroxyalkyl Methacrylates (HEMA) | 10,404 | 11,459 | 12,830 |
| Acrylate Esters (HEA) | 949 | 760 | 1,007 |
| Dimethly Benzene Methanol | 4,672 | 4,116 | 7,627 |
| Tributyl Amine Derivatives (TBA) | 150 | 118 | 173 |
| Acetophenone (CHAP, DMAP, etc.) | 949 | 644 | 1,070 |
| Acrylic Acids (other than EHA) | 0 | 120 | 58 |
| Organic Acids | 0 | 21 | 136 |
| BHT | 456 | 616 | 1,466 |
| Styrene & derivatives | 1,437 | 965 | 1,311 |
| Hydrocarbons, others | 27,333 | 16,619 | 23,344 |
| Totals | 46,350 | 35,439 | 49,475 |

Note: a value of 0 is below the threshold limit of the test equipment.

Thus, the trend from the above table demonstrates that an entire idle spindle motor 20 will outgas more compounds than an idle spindle motor that is partially concealed within a spindle motor fixture 70. Likewise, an operating spindle motor 20 will typically outgas more compounds than an idle spindle motor 20 when both are fitted within the fixture 70. This is particularly true of the more aggressive compounds such as Glycol Dimethacrylates (TGDMA), acrylic esters (HEA), BHT and acetophenones such as DMAP. It is aggressive compounds such as these that drive manufacturers are primarily concerned about since these compounds are most likely to cause a head disc crash.

The spindle motor fixture 70 thus enhances the ability to perform outgassing tests on spindle motors 20 by accurately simulating the environment to which the spindle motor 20 is exposed within a disc drive 26. The inert material (preferably Teflon) which comprises the forms the interior chamber 80 of the fixture 70 prevents the fixture 70 from outgassing any compounds of its own during the test and further prevents the fixture 70 from reacting with any compounds outgassed by the spindle motor 20. Indeed, even the stainless steel mounting ring 100 is preferably recessed within the exterior bottom surface 88 of the fixture 70 to prevent the ring 100 from being exposed to the interior of the test chamber 130.

While the spindle motor fixture 70 is shown in one preferred embodiment with the dynamic headspace outgassing system described in the parent application, it is understood that the benefits of the fixture 70 (i.e., increase accuracy of the test results) may be realized with any outgassing system that is capable of testing spindle motors 20 in their entirety.

In summary, the preferred embodiment exemplary of the invention and disclosed herein is directed to an apparatus (such as 70) for retaining a spindle motor (such as 20) during an outgassing test, the spindle motor including an annular base (such as 22) and a hub (such as 28) adapted to rotate relative to the annular base (such as 22). The apparatus (such as 70) includes a body (such as 72) defining an interior chamber (such as 80) adapted to receive the annular base (such as 22), the body (such as 72) further defining an annular rim (such as 86) surrounding an open upper end of the interior chamber (such as 80). Fasteners (such as 96) are adapted to secure the spindle motor (such as 20) to the annular rim (such as 86) to form a substantially airtight seal within the interior chamber (such as 80).

In another preferred embodiment of the present invention, the body (such as 72) is formed from an inert material such as Teflon.

In another preferred embodiment of the present invention, the annular base (such as 22) of the spindle motor (such as 20) includes a protruding annular flange (such as 46) having holes (such as 94) formed therein. The annular rim (such as 86) also includes holes (such as 92) aligned with the holes (such as 94) in the annular flange (such as 46) for receiving the fasteners (such as 96).

In another preferred embodiment of the present invention, the holes (such as 92) in the annular rim (such as 86) extend through the body (such as 72) to a bottom surface (such as 88) of the body. An annular ring (such as 100) attached to the bottom surface (such as 88) of the body (such as 72) below the annular rim (such as 86) includes a base (such as 102) and posts (such as 104) extending vertically upward from the base (such as 102) through the holes (such as 92) in the body (such as 72) to act as anchors for the fasteners (such as 96).

In another preferred embodiment of the present invention, the annular ring base (such as 102) and the posts (such as 104) are formed from stainless steel. Each post (such as 104) includes a hollow threaded interior (such as 106) to receive an end of one of the fasteners (such as 96).

In another preferred embodiment of the present invention, the bottom surface (such as 88) of the body (such as 72) includes an annular groove (such as 90). The annular ring base (such as 102) is fitted within the annular groove (such as 90) to recess the annular ring base (such as 102) within the bottom surface (such as 88) of the body (such as 72).

In another preferred embodiment of the present invention, the spindle motor (such as 20) includes an electrical connector (such as 52) attached to the annular base (such as 22) of the spindle motor. An electrical pad (such as 112) is attached within the interior chamber (such as 80) for contacting the electrical connector (such as 52). An electrical wire (such as 116) is attached at one end to the electrical pad (such as 112), and a second end of the electrical wire (such as 116) extends outside of the interior chamber (such as 80) through an opening (such as 122) formed in the body (such as 72).

In another preferred embodiment of the present invention, a sheath (such as 124) formed from an inert material such as Teflon covers a portion of the electrical wire (such as 116) extending outside of the interior chamber (such as 80).

In another preferred embodiment of the present invention, the electrical connector (such as 52) is attached to an outer surface of the annular base (such as 22) of the spindle motor (such as 20). The body (such as 72) defines a notched region (such as 110) within the interior chamber (such as 80). The notched region (such as 110) extends to the annular rim (such as 86) and is adapted to receive the electrical connector (such as 52) when the annular base (such as 22) of the spindle motor (such as 20) is inserted within the interior chamber (such as 80). The electrical pad (such as 112) is located within the notched region (such as 110).

In another preferred embodiment of the present invention, the electrical pad (such as 112) is fixed to a circuit board (such as 114), and the circuit board is attached within a bottom portion of the notched region (such as 110).

A further preferred embodiment of the present invention includes apparatus for collecting outgassed compounds from a spindle motor (such as 20), the spindle motor including an annular base (such as 22) and a hub (such as 28) adapted to rotate relative to the annular base (such as 22). The apparatus includes a body (such as 72) defining an interior chamber (such as 80) adapted to receive the annular base (such as 22), the body (such as 72) formed from an inert material and further defining an annular rim (such as 86) surrounding an open upper end of the interior chamber (such as 80). Fasteners (such as 96) are adapted to secure the spindle motor (such as 20) to the annular rim (such as 86) to form a substantially airtight seal within the interior chamber (such as 80). A test container (such as 132) defines an interior volume (such as 130) to receive the body (such as 72) and the spindle motor (such as 20).

In another preferred embodiment of the present invention, the spindle motor (such as 20) includes an electrical connector (such as 52) attached to the annular base (such as 22) of the spindle motor. An electrical pad (such as 112) attached within the interior chamber (such as 80) contacts the electrical connector (such as 52). An electrical wire (such as 116) attached at one end to the electrical pad (such as 112). A second end of the electrical wire (such as 116) extends outside of the interior chamber (such as 80) of the body (such as 72) through an opening (such as 122) formed in the body (such as 72) and outside of the interior volume (such as 130) of the test container (such as 132) through an opening formed in the test container.

In another preferred embodiment of the present invention, a combination power source and motor controller (such as 120) attached to the second end of the electrical wire (such as 116) operates the spindle motor (such as 20).

In another preferred embodiment of the present invention, a sheath (such as 124) formed from an inert material covers a portion of the electrical wire (such as 116) extending outside of the interior chamber (such as 80) of the body (such as 72) and inside the interior volume (such as 130) of the test container (such as 132).

In another preferred embodiment of the present invention, the electrical connector (such as 52) is attached to an outer surface of the annular base (such as 22) of the spindle motor (such as 20). The body (such as 72) defines a notched region (such as 110) within the interior chamber (such as 80). The notched region (such as 110) extends to the annular rim (such as 86) and is adapted to receive the electrical connector (such as 52) when the annular base (such as 22) of the spindle motor (such as 20) is inserted within the interior chamber (such as 80). The electrical pad (such as 112) is located within the notched region (such as 110).

In another preferred embodiment of the present invention, a bottom surface (such as 88) of the body (such as 72) includes an annular groove (such as 90) positioned below the annular rim (such as 86). A stainless steel annular ring (such as 100) is fitted within the annular groove (such as 90), and the annular ring (such as 100) includes posts (such as 104) extending vertically upward through the body (such as 72) to act as anchors for the fasteners (such as 96).

A further preferred embodiment of the present invention includes apparatus for collecting outgassed compounds from a spindle motor (such as 20), the spindle motor having an annular base (such as 22) and a hub (such as 28) adapted to rotate relative to the annular base. The apparatus includes a test container (such as 132) and means for retaining the spindle motor (such as 20) in the test container (such as 132) and for preventing the annular base (such as 22) from outgassing compounds within the test container (such as 132).

In another preferred embodiment of the present invention, the apparatus includes means for providing power to the spindle motor (such as 20) to operate the spindle motor within the test container (such as 132).

It will be clear that the present invention is well adapted to attain the ends and advantages mentioned as well as those inherent therein. While a presently preferred embodiment has been described for purposes of this disclosure, numerous changes may be made which will readily suggest themselves to those skilled in the art and which are encompassed in the spirit of the invention disclosed and as defined in the appended claims.

What is claimed is:

1. An apparatus for retaining a spindle motor during an outgassing test, the spindle motor including an annular base and a hub adapted to rotate relative to the annular base, the apparatus comprising:

a body defining an interior chamber adapted to receive the annular base, the body further defining an annular rim surrounding an open upper end of the interior chamber; and fasteners adapted to secure the spindle motor to the annular rim to form a substantially airtight seal within the interior chamber.

2. An apparatus as defined in claim 1, wherein the body is formed from an inert material.

3. An apparatus as defined in claim 2, wherein the body is formed from Teflon.

4. An apparatus as defined in claim 2, wherein the annular base of the spindle motor includes a protruding annular flange having holes formed therein, and wherein:

the annular rim includes holes aligned with the holes in the annular flange for receiving the fasteners.

5. An apparatus as defined in claim 4, wherein the holes in the annular rim extend through the body to a bottom surface of the body, the apparatus further comprising:

an annular ring attached to the bottom surface of the body below the annular rim, the annular ring including a base and posts extending vertically upward from the base through the holes in the body to act as anchors for the fasteners.

6. An apparatus as defined in claim 5, wherein:

the annular ring base and the posts are formed from stainless steel; and each post includes a hollow threaded interior to receive an end of one of the fasteners.

7. An apparatus as defined in claim 6, wherein:

the bottom surface of the body includes an annular groove; and the annular ring base is fitted within the annular groove to recess the annular ring base within the bottom surface of the body.

8. An apparatus as defined in claim 2, wherein the spindle motor includes an electrical connector attached to the annular base of the spindle motor, the apparatus further comprising:

an electrical pad attached within the interior chamber for contacting the electrical connector; and an electrical wire attached at one end to the electrical pad, the electrical wire including a second end extending outside of the interior chamber through an opening formed in the body.

9. An apparatus as defined in claim 8 further comprising:

a sheath formed from an inert material, the sheath covering a portion of the electrical wire extending outside of the interior chamber.

10. An apparatus as defined in claim 9, wherein the sheath is formed from Teflon.

11. An apparatus as defined in claim 8, wherein the electrical connector is attached to an outer surface of the annular base of the spindle motor, and wherein:

the body defines a notched region within the interior chamber, the notched region extending to the annular rim and adapted to receive the electrical connector when the annular base of the spindle motor is inserted within the interior chamber; and the electrical pad is located within the notched region.

12. An apparatus as defined in claim 11 wherein:

the electrical pad is fixed to a circuit board; and the circuit board is attached within a bottom portion of the notched region.

13. Apparatus for collecting outgassed compounds from a spindle motor, the spindle motor including an annular base and a hub adapted to rotate relative to the annular base, the apparatus comprising:

a body defining an interior chamber adapted to receive the annular base, the body formed from an inert material and further defining an annular rim surrounding an open upper end of the interior chamber;

fasteners adapted to secure the spindle motor to the annular rim to form a substantially airtight seal within the interior chamber; and a test container defining an interior volume to receive the body and the spindle motor.

14. An apparatus as defined in claim 13, wherein the spindle motor includes an electrical connector attached to the annular base of the spindle motor, the apparatus further comprising:

an electrical pad attached within the interior chamber for contacting the electrical connector; and an electrical wire attached at one end to the electrical pad, the electrical wire including a second end extending outside of the interior chamber of the body through an opening formed in the body and outside of the interior volume of the test container through an opening formed in the test container.

15. An apparatus as defined in claim 14 further comprising:

a combination power source and motor controller attached to the second end of the electrical wire to operate the spindle motor.

16. An apparatus as defined in claim 15 further comprising:

a sheath formed from an inert material, the sheath covering a portion of the electrical wire extending outside of the interior chamber of the body and inside the interior volume of the test container.

17. An apparatus as defined in claim 16, wherein the electrical connector is attached to an outer surface of the annular base of the spindle motor, and wherein:

the body defines a notched region within the interior chamber, the notched region extending to the annular rim and adapted to receive the electrical connector when the annular base of the spindle motor is inserted within the interior chamber; and the electrical pad is located within the notched region.

18. An apparatus as defined in claim 16, wherein a bottom surface of the body includes an annular groove positioned below the annular rim, the apparatus further comprising:

a stainless steel annular ring fitted within the annular groove, the annular ring including posts extending vertically upward through the body to act as anchors for the fasteners.

19. Apparatus for collecting outgassed compounds from a spindle motor, the spindle motor having an annular base and a hub adapted to rotate relative to the annular base, the apparatus comprising:

a test container; and means for retaining the spindle motor in the test container and for preventing the annular base from outgassing compounds within the test container.

20. Apparatus as defined in claim 19 further comprising:

means for providing power to the spindle motor to operate the spindle motor within the test container.

* * * * *